United States Patent
Park et al.

(10) Patent No.: US 9,326,732 B2
(45) Date of Patent: May 3, 2016

(54) ELECTROCARDIOGRAM SENSOR AND METHOD OF PROCESSING SIGNALS USING THE SAME

(71) Applicant: Samsung Electronics Co., Ltd., Suwon-Si, Gyeonggi-Do (KR)

(72) Inventors: Sang Wook Park, Hwaseong-si (KR); Myoung Oh Ki, Seoul (KR); Yun Cheol Han, Yongin-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 14/598,918

(22) Filed: Jan. 16, 2015

(65) Prior Publication Data

US 2015/0223758 A1 Aug. 13, 2015

(30) Foreign Application Priority Data

Feb. 13, 2014 (KR) .......................... 10-2014-0016898

(51) Int. Cl.
*A61B 5/04* (2006.01)
*A61B 5/00* (2006.01)
*A61B 5/0408* (2006.01)

(52) U.S. Cl.
CPC ............. *A61B 5/7203* (2013.01); *A61B 5/0006* (2013.01); *A61B 5/04002* (2013.01); *A61B 5/0408* (2013.01); *A61B 5/04012* (2013.01)

(58) Field of Classification Search
CPC ............. A61B 5/7203; A61B 5/72037; A61B 5/7225; A61B 5/7221; A61B 5/04012; A61B 5/0006
See application file for complete search history.

(56) References Cited

U.S. PATENT DOCUMENTS

| | | |
|---|---|---|
| 5,617,060 A | 4/1997 | Wilson et al. |
| 6,510,339 B2 | 1/2003 | Kovtun et al. |
| 6,516,185 B1 | 2/2003 | MacNally |
| 7,110,734 B2 | 9/2006 | Mohindra |
| 7,233,780 B2 | 6/2007 | Franca-Neto |
| 7,236,056 B2 | 6/2007 | Chang et al. |
| 7,302,022 B2 | 11/2007 | Kim et al. |
| 7,372,925 B2 | 5/2008 | Pipilos |
| 7,532,873 B2 | 5/2009 | Mohindra |
| 7,695,085 B2 | 4/2010 | Bae et al. |
| 8,212,942 B2 | 7/2012 | Gu et al. |
| 2008/0119716 A1* | 5/2008 | Boric-Lubecke .... A61B 5/0205 600/407 |
| 2010/0075624 A1 | 3/2010 | Shanan |
| 2010/0237851 A1* | 9/2010 | Coster ................... G01R 27/28 324/76.19 |
| 2010/0246643 A1* | 9/2010 | Lim ......................... H04B 1/69 375/147 |
| 2011/0286495 A1 | 11/2011 | Seller et al. |

* cited by examiner

*Primary Examiner* — Robert N Wieland

(74) *Attorney, Agent, or Firm* — Harness, Dickey & Pierce, P.L.C.

(57) ABSTRACT

An electrocardiogram (ECG) sensor includes an analog front end device configured to remove a DC offset in a first ECG signal received from a measuring electrode, and adjust a gain amplification value based on the first ECG signal. The analog front end device is configured to output an adjusted first ECG signal, the adjusted first ECG signal being based on the adjusted gain amplification value and the removed DC offset in the first ECG signal. The ECG sensor includes a digital signal processor configured to analyze and process the adjusted first ECG signal based on an algorithm and to output information. The analog front end device is configured to remove the DC offset in the first ECG signal during a first period, and remove a DC offset in a second ECG signal and simultaneously adjust a gain amplification value for the second ECG signal during a second period.

19 Claims, 5 Drawing Sheets

ELECTROCARDIOGRAM SENSOR AND METHOD OF PROCESSING SIGNALS USING THE SAME

CROSS-REFERENCE TO RELATED APPLICATIONS

This application claims priority under 35 U.S.C.§119(a) from Korean Patent Application No. 10-2014-0016898 filed on Feb. 13, 2014, the disclosure of which is hereby incorporated by reference in its entirety.

BACKGROUND

At least one example embodiment of the inventive concepts relates to an electrocardiogram (ECG) sensor, and more particularly, to an ECG sensor capable of performing DC offset and gain adjustment at one time and/or a method of processing a signal using the same.

An ECG sensor is usually used to measure an ECG of a patient's heart. The ECG sensor processes and analyzes a signal measured from an electrode directly contacting a patient's body and the patient's physical condition can be evaluated using ECG signals output from the ECG sensor.

Recently, as people's interest in health increases, it is desired to display or transmit a patient's physical condition based on an ECG signal measured by an ECG sensor to an external device through a connection to a communication system. This enables fast treatment, early diagnosis, and prevention. However, when motion artifacts or DC offsets are introduced to the ECG signal measured by the ECG sensor, it is difficult to correctly analyze an original signal.

SUMMARY

According to at least one example embodiment of the inventive concepts, an electrocardiogram (ECG) sensor includes an analog front end device configured to remove a DC offset in a first ECG signal received from a measuring electrode, and adjust a gain amplification value based on the first ECG signal. The analog front end device is configured to output an adjusted first ECG signal, the adjusted first ECG signal being based on the adjusted gain amplification value and the removed DC offset in the first ECG signal. The ECG sensor includes a digital signal processor configured to analyze and process the adjusted first ECG signal based on an algorithm and to output information. The analog front end device is configured to remove the DC offset in the first ECG signal during a first period, and remove a DC offset in a second ECG signal and simultaneously adjust a gain amplification value for the second ECG signal during a second period.

According to at least one example embodiment the analog front end device (AFE) comprises an amplifier configured to receive the first ECG signal from the measuring electrode and amplify the first ECG signal based on the gain amplification value for the first ECG signal. The AFE includes an analog-to-digital converter configured to perform analog-to-digital conversion on the amplified first ECG signal and output a digital ECG signal. The AFE includes an automatic gain controller configured to detect a peak value of the digital ECG signal and to adjust the gain amplification value for the adjusted first ECG signal based on the peak value.

According to at least one example embodiment, the AFE further comprises a DC offset calculator configured to calculate a mean value of the digital ECG signal, calculate a DC offset with respect to the mean value, and output the DC offset calculated with respect to the mean value. The AFE includes a digital-to-analog converter configured to perform digital-to-analog conversion on the DC offset output from the DC offset calculator to output an analog DC offset. The amplifier is configured to remove the DC offset from the first ECG signal based on the analog DC offset.

According to at least one example embodiment, the DC offset calculator is configured to determine whether the DC offset calculated with respect to the mean value is in a first reference range.

According to at least one example embodiment, the DC offset calculator is configured to output a bit value corresponding to a changed DC offset with respect to the digital ECG signal if the DC offset calculated with respect to the mean value is not in the first reference range, the bit value being output to the digital-to-analog converter.

According to at least one example embodiment, the automatic gain controller is configured to detect the peak value of the digital ECG signal and to determine whether the detected peak value is in a second reference range.

According to at least one example embodiment, the automatic gain controller is configured to output a bit value corresponding to a changed gain amplification value with respect to the digital ECG signal if the detected peak value is not in the second reference range, the bit value being output to the amplifier.

According to at least one example embodiment the automatic gain controller comprises a timer configured to count a time during which the adjusted gain amplification value is applied to one of the first and second ECG signals.

According to at least one example embodiment the ECG sensor includes a radio frequency (RF) module configured to transmit the information detected by the digital signal processor via a wireless connection.

According to at least one example embodiment a method of processing a signal using an electrocardiogram (ECG) sensor includes calculating, by the ECG sensor, a DC offset in an initial ECG signal received from a measuring electrode during a first period. The method includes removing, by the ECG sensor, a DC offset from a first ECG signal received during a second period, the removing being based on the calculated DC offset in the initial ECG signal. The method includes calculating, by the ECG sensor, a DC offset in a second ECG signal received during the second period and adjusting a gain amplification value for the second ECG signal.

According to at least one example embodiment, the calculating the DC offset in the second ECG signal comprises calculating a DC offset with respect to a mean value of the second ECG signal, determining whether the DC offset is in a first reference range, and outputting a bit value corresponding to a decreased or increased DC offset with respect to the second ECG signal if the DC offset is not in the first reference range.

According to at least one example embodiment, the adjusting the gain amplification value for the second ECG signal comprises detecting a peak value of the second ECG signal, determining whether the peak value is in a second reference range, and outputting a bit value corresponding to a decreased or increased gain amplification value with respect to the second ECG signal if the peak value is not in the second reference range.

According to at least one example embodiment, the calculating the DC offset in the second ECG signal and the adjusting the gain amplification value for the second ECG signal are performed simultaneously and repeatedly while the ECG sensor is operating.

According to at least one example embodiment, a device, comprises an analog front end device configured to calculate a first DC offset in a first ECG signal received from a measuring electrode, and remove a second DC offset in a second ECG signal based on the calculated first DC offset. The second ECG signal may be received subsequent to the first ECG signal. The analog front end device may be configured to adjust an amplitude of the second ECG signal in response to an enable signal, the enable signal being controlled based on the calculated first DC offset.

According to at least one example embodiment, the analog front end device is configured to adjust the amplitude of the second ECG signal such that a peak value is within a first reference range.

According to at least one example embodiment, the analog front end device is configured to calculate the first DC offset such that the first DC offset is within a second reference range.

According to at least one example embodiment, wherein the analog front end device is configured to calculate the second DC offset based on a mean value of the second ECG signal.

According to at least one example embodiment, wherein the analog front end device is configured to remove a third DC offset in a third ECG signal based on the calculated second DC offset, the third ECG signal being received subsequent to the second ECG signal.

BRIEF DESCRIPTION OF THE DRAWINGS

The above and other features and advantages of the inventive concepts will become more apparent by describing in detail example embodiments thereof with reference to the attached drawings in which.

DETAILED DESCRIPTION OF EXAMPLE EMBODIMENTS

Figure 1:
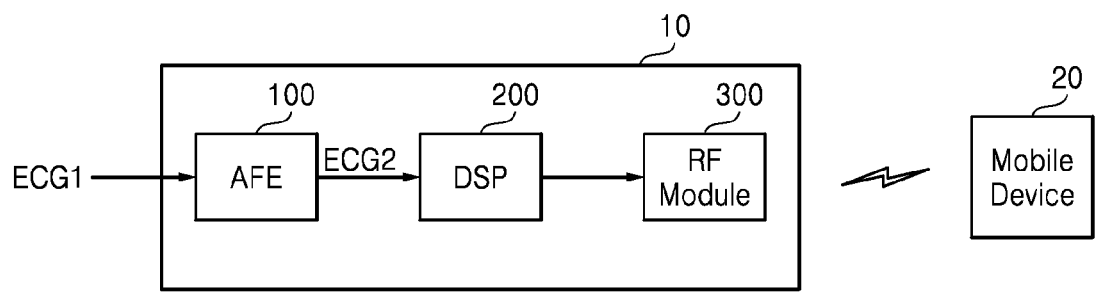
FIG. 1 is a schematic block diagram of an electrocardiogram (ECG) sensor according to at least one example embodiment of the inventive concepts.

Inventive concepts will now be described more fully with reference to the accompanying drawings, in which example embodiments of are shown. These example embodiments are provided so that this disclosure will be thorough and complete, and will fully convey inventive concepts of to those skilled in the art. Inventive concepts may be embodied in many different forms with a variety of modifications, and a few embodiments will be illustrated in drawings and explained in detail. However, this should not be construed as being limited to example embodiments set forth herein, and rather, it should be understood that changes may be made in these example embodiments without departing from the principles and spirit of inventive concepts, the scope of which are defined in the claims and their equivalents. Like numbers refer to like elements throughout. In the drawings, the thicknesses of layers and regions are exaggerated for clarity.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Specific details are provided in the following description to provide a thorough understanding of example embodiments. However, it will be understood by one of ordinary skill in the art that example embodiments may be practiced without these specific details. For example, systems may be shown in block diagrams so as not to obscure example embodiments in unnecessary detail. In other instances, well-known processes, structures and techniques may be shown without unnecessary detail in order to avoid obscuring example embodiments.

In the following description, illustrative embodiments will be described with reference to acts and symbolic representations of operations (e.g., in the form of flow charts, flow diagrams, data flow diagrams, structure diagrams, block diagrams, etc.) that may be implemented as program modules or functional processes include routines, programs, objects, components, data structures, etc., that perform particular tasks or implement particular abstract data types and may be implemented using existing hardware in existing electronic systems (e.g., electronic imaging systems, image processing systems, digital point-and-shoot cameras, personal digital assistants (PDAs), smartphones, tablet personal computers (PCs), laptop computers, etc.). Such existing hardware may include one or more Central Processing Units (CPUs), digital signal processors (DSPs), application-specific-integrated-circuits (ASICs), field programmable gate arrays (FPGAs) computers or the like.

Although a flow chart may describe the operations as a sequential process, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible or non-transitory machine readable mediums for storing information. The term "computer-readable medium" may include, but is not limited to, portable or fixed storage devices, optical storage devices, and various other tangible or non-transitory mediums capable of storing, containing or carrying instruction(s) and/or data.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, a processor or processors may be programmed to perform the necessary tasks, thereby being transformed into special purpose processor(s) or computer(s).

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "includes", "including", "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which inventive concepts belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term "and/or" includes any and all combinations of one or more of the associated listed items. Expressions such as "at least one of," when preceding a list of elements, modify the entire list of elements and do not modify the individual elements of the list.

FIG. 1 is a schematic block diagram of an electrocardiogram (ECG) sensor 10 according to at least one example embodiment of the inventive concepts. Referring to FIG. 1, the ECG sensor 10 may detect an ECG signal generated from parts (e.g., chest, arms, and legs) of a person's body by the person's heart and may transmit the ECG signal to a mobile device 20. The ECG sensor 10 may include an analog front end device (AFE) 100, a digital signal processor (DSP) 200, and a radio frequency (RF) module 300.

The AFE 100 may remove a DC offset from an ECG signal ECG1 received from a measuring electrode attached to a body, may adjust a gain amplification value of the signal ECG1, and may output a gain amplification value-adjusted ECG signal ECG2. The DSP 200 may analyze and process the ECG signal ECG2 from the AFE 100 based on a desired (or alternatively, predetermined) algorithm and may detect and output information based on the analysis and processing. The RF module 300 may transmit the information output from the DSP 200 to the mobile device 20 via a wireless connection.

The mobile device 20 may be a device, such as an ECG tester, a smart phone, a notebook computer, etc., that can communicate with the ECG sensor 10 in a wireless connection. The mobile device 20 may output the information received from the ECG sensor 10 in a form of image or voice that can be recognized by a user. In other words, the user is allowed to check the state of a patient's heart in real time based on the information output by the mobile device 20.

Figure 2:
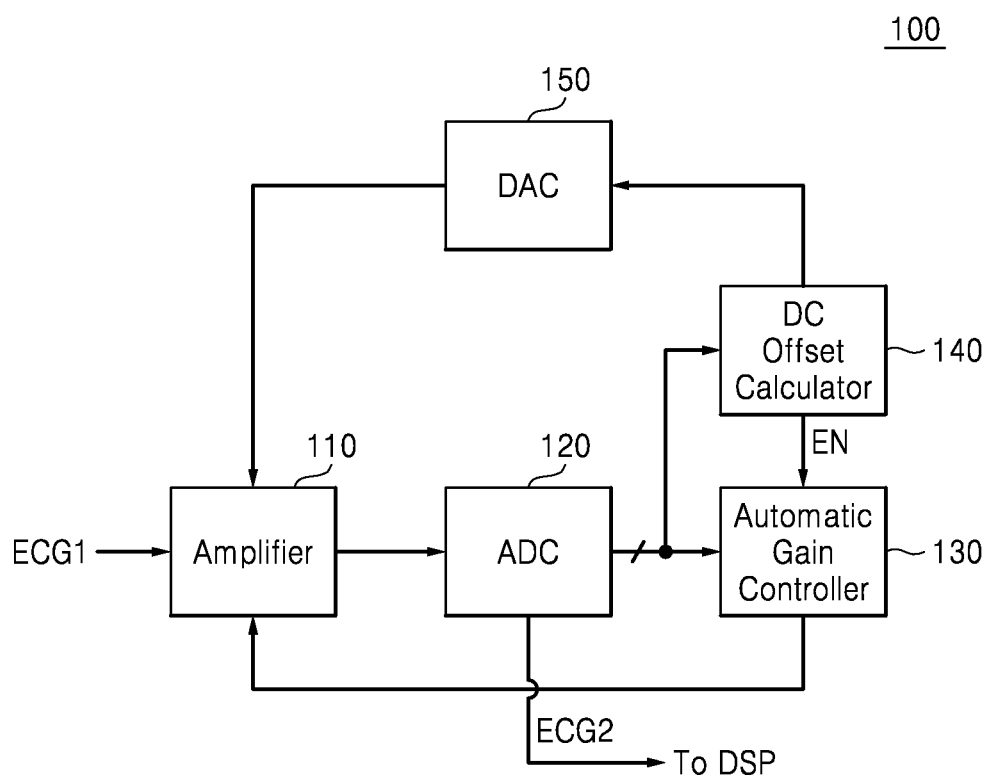
FIG. 2 is a block diagram of an analog front end device (AFE) according to at least one example embodiment of the inventive concepts.

FIG. 2 is a block diagram of the AFE 100 according to at least one example embodiment of the inventive concepts. Referring to FIG. 2, the AFE 100 may include an amplifier 110, an analog-to-digital converter (ADC) 120, an automatic gain controller 130, a DC offset calculator 140, and a digital-to-analog converter (DAC) 150.

The amplifier 110 may receive the ECG signal ECG1 from a measuring electrode (e.g., on a patient's body) and may amplify the gain of the ECG signal ECG1 based on a gain amplification value. The ADC 120 may perform analog-to-digital conversion on the gain-amplified ECG signal and may output a digital ECG signal.

The automatic gain controller 130 may detect a peak value in the digital ECG signal output from the ADC 120 based on an enable signal EN and may output a gain amplification value that has been adjusted based on the peak value to the amplifier 110. The amplifier 110 may adjust the gain of the ECG signal ECG1 received from the measuring electrode based on the gain amplification value output from the automatic gain controller 130.

The automatic gain controller 130 may include a timer (not shown) to count a desired (or alternatively, predetermined) time so that the adjusted gain amplification value is applied when the gain of the ECG signal ECG1 received from the measuring electrode is desired to be adjusted. While the timer is performing a counting operation, the automatic gain controller 130 may not perform an operation of adjusting the gain amplification value with respect to ECG signals output from the ADC 120 but may instead continuously output the same gain amplification value that has been adjusted.

The DC offset calculator 140 may calculate a DC offset in the digital ECG signal output from the ADC 120 and may output the DC offset. The DC offset calculator 140 may output the enable signal EN for adjusting the gain amplification value of an ECG signal to the automatic gain controller 130 after calculating and outputting the DC offset in the ECG signal during the initial operation of the ECG sensor 10.

The DAC 150 may perform digital-to-analog conversion on the DC offset output from the DC offset calculator 140 and may output an analog DC offset to the amplifier 110. The amplifier 110 may remove the DC offset from the ECG signal ECG1 received from the measuring electrode based on the analog DC offset to send an ECG signal ECG2 to ADC 120. The ADC 120 may output the ECG signal ECG2, which corresponds to a result of removing the DC offset from the ECG signal ECG1 and adjusting the gain of the ECG signal ECG1, to the DSP 200.

Figure 3:
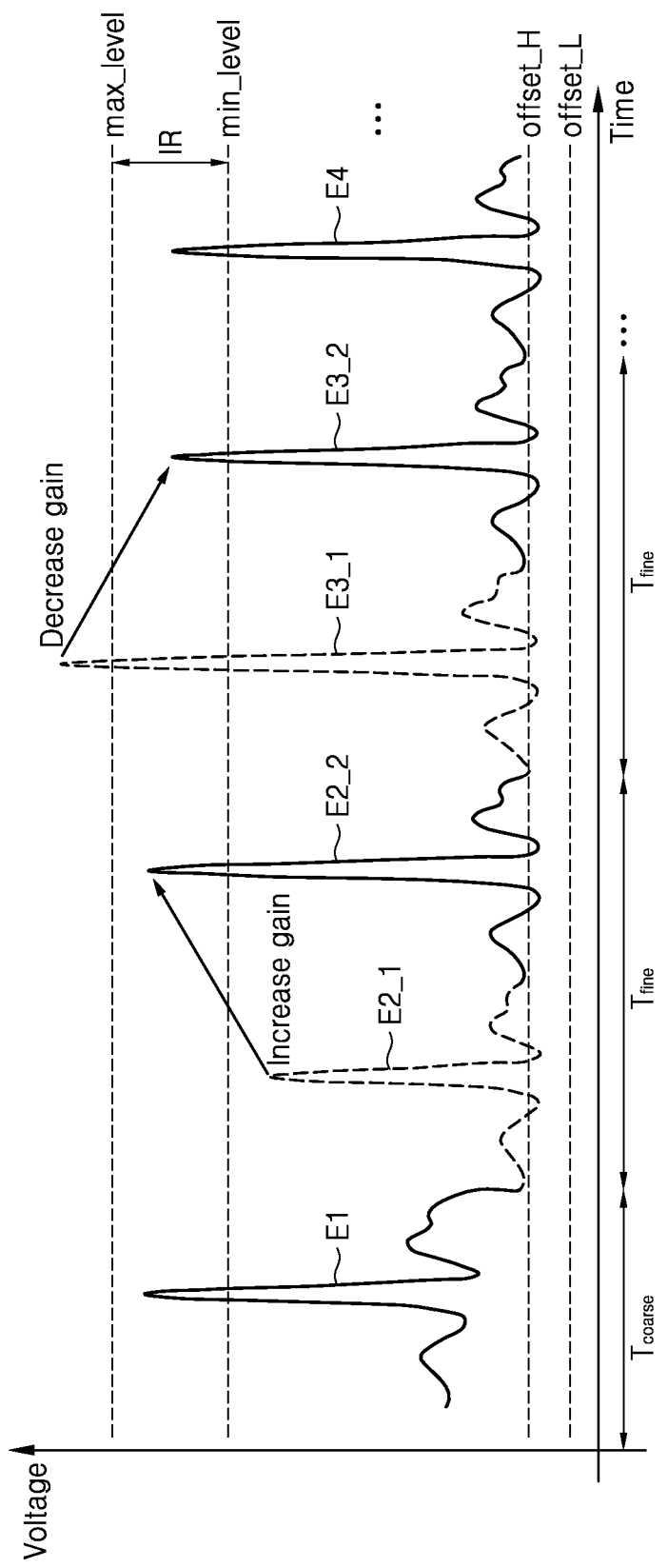
FIG. 3 is a diagram for explaining an operation of the AFE illustrated in FIG. 2.

FIG. 3 is a diagram for explaining an operation of the AFE 100 illustrated in FIG. 2. Referring to FIGS. 2 and 3, the AFE 100 may remove a DC offset from an ECG signal E1 received from a measuring electrode during a first period $T_{coarse}$, and then may remove a DC offset from ECG signals E2, E3, and E4 received during a second period $T_{fine}$ and simultaneously adjust a gain amplification value of ECG signals E2, E3, and E4.

The first period $T_{coarse}$ and the second period $T_{fine}$ may be the same duration. However, while the first period $T_{coarse}$ is for removing a DC offset from an ECG signal received from a measuring electrode, the second period $T_{fine}$ is for removing a DC offset from a subsequent ECG signal received after DC offset removing is once performed in $T_{coarse}$ and for simultaneously adjusting the gain amplification value of the subsequent ECG signal.

The DC offset calculator 140 may calculate a DC offset in the ECG signal E1 received during the first period $T_{coarse}$ and may output a bit value corresponding to the DC offset to the DAC 150. Thereafter, the DC offset calculator 140 may calculate a mean value of the ECG signal E2 received during the second period $T_{fine}$, may calculate a DC offset for the mean value, and may determine whether the DC offset is in a first reference range between offset_L and offset_H.

When the DC offset is not in the first reference range between offset_L and offset_H, the DC offset calculator 140 may output a bit value corresponding to the DC offset that has been decreased or increased with respect to the ECG signal E2 to the DAC 150. At this time, a DC offset is calculated with respect to the mean value of an ECG signal received during the second period $T_{fine}$. The DC offset calculated during the second period $T_{fine}$ may be less than the DC offset calculated with respect to an ECG signal received during the first period $T_{coarse}$.

In other words, after a DC offset is removed from an ECG signal received during the second period $T_{fine}$ based on a DC offset calculated during the first period $T_{coarse}$, the DC offset calculator 140 may calculate and output a DC offset with respect to a mean value of an ECG signal E2_1 and the automatic gain controller 130 may output an adjusted gain amplification value with respect to the ECG signal E2_1. At this time, the automatic gain controller 130 may determine whether a peak value of the ECG signal E2_1 is in a second reference range IR and may output a bit value, which corresponds to a gain amplification value that has been decreased or increased with respect to the ECG signal E2_1 based on the determination result, to the amplifier 110.

When the peak value is lower than a first reference value min_level, the automatic gain controller 130 may output a bit value for increasing the gain amplification value to the amplifier 110 and may output an ECG signal E2_2 obtained after a gain has been increased to the DSP 200. In addition, when a peak value of an ECG signal E3_1 is higher than a second reference value max level, the automatic gain controller 130 may output a bit value for decreasing the gain amplification value to the amplifier 110 and may output an ECG signal E3_2 obtained after a gain has been decreased to the DSP 200.

Consequently, when the above-described procedure is repeated during the second period $T_{fine}$, the DC offset may be in the first reference range between offset_L and offset_H and the peak value of an ECG signal E4 may be in the second reference range IR, as shown in the ECG signal E4. As a result, the magnitude of an ECG signal that has been measured may be maintained in a desired (or alternatively, predetermined) range, so that a user is allowed to get more accurate information.

Figure 4:
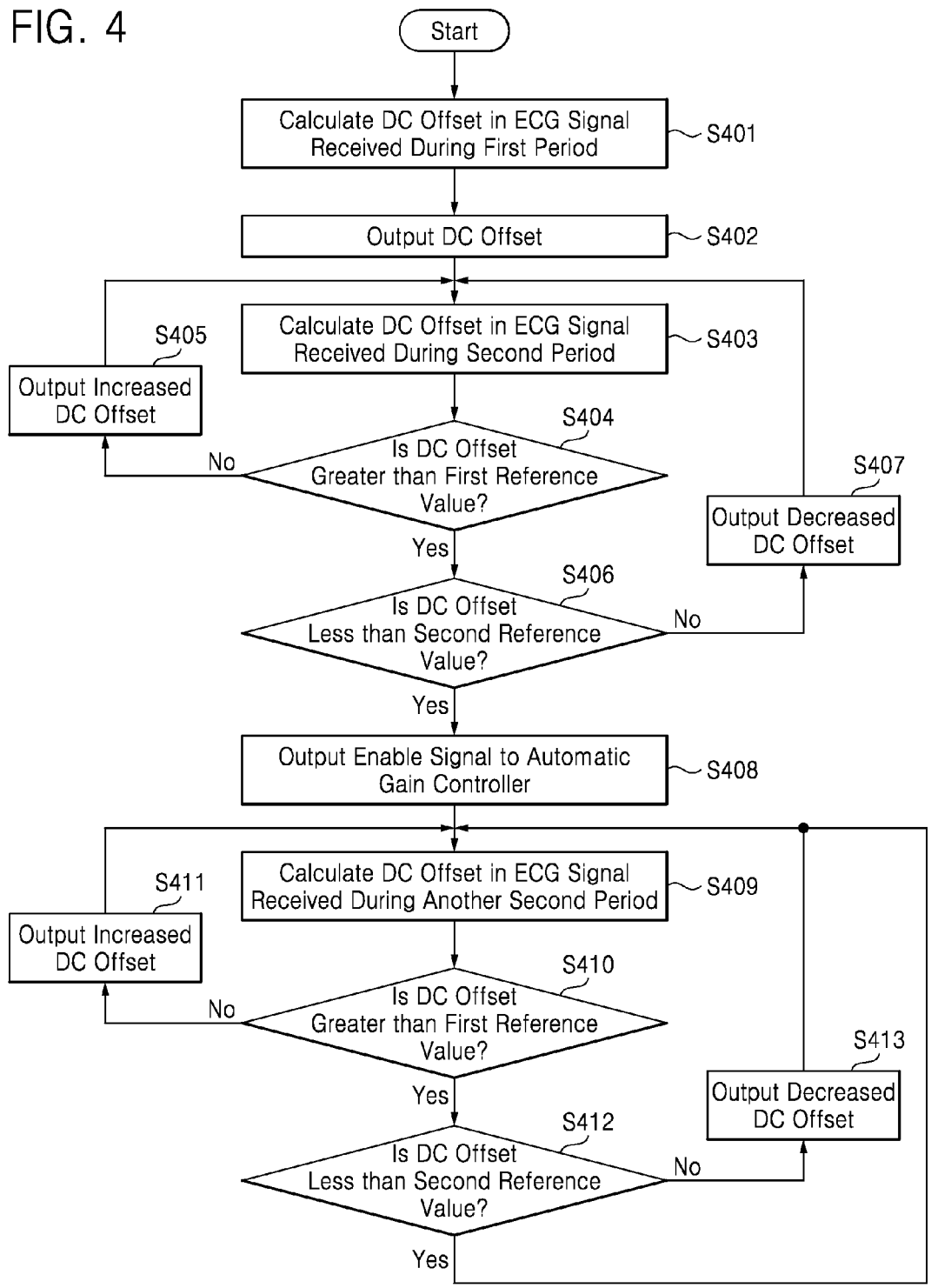
FIG. 4 is a flowchart of a method of processing a signal using a DC offset calculator illustrated in FIG. 2 according to at least example embodiment of the inventive concepts.

FIG. 4 is a flowchart of a method of processing a signal using the DC offset calculator 140 illustrated in FIG. 2 according to at least one example embodiment of the inventive concepts. When an ECG signal is received from the ADC 120 after the ECG sensor 10 starts, the DC offset calculator 140 may perform the method illustrated in FIG. 4.

Referring to FIGS. 2 through 4, the DC offset calculator 140 calculates a DC offset in an ECG signal received during the first period $T_{coarse}$ in operation S401 and outputs the DC offset to the DAC 150 in operation S402. The DC offset calculator 140 calculates a DC offset with respect to a mean value of an ECG signal received during the second period $T_{fine}$ in operation S403 and determines whether the DC offset is greater than a first reference value offset L in operation S404.

In operation S405, when the DC offset is less than the first reference value offset_L, the DC offset calculator 140 outputs a bit value corresponding to a DC offset that has been increased with respect to the mean value of the ECG signal to the DAC 150. When the DC offset is determined as greater than the first reference value offset_L in operation S405, the DC offset calculator 140 determines whether the DC offset is less than a second reference value offset_H in operation S406.

In operation S407, when the DC offset is greater than the second reference value offset_H, the DC offset calculator 140 outputs a bit value corresponding to a DC offset that has been decreased with respect to the mean value of the ECG signal to the DAC 150. In operation S408, when the DC offset is determined as less than the second reference value offset_H in operation S406, the DC offset calculator 140 outputs the enable signal EN to the automatic gain controller 130 in order to adjust the gain of the ECG signal.

Thereafter, in operation S409, the DC offset calculator 140 calculates a DC offset with respect to the mean value of an ECG signal received during another second period $T_{fine}$. In operation S410, the DC offset calculator 140 determines whether the DC offset is higher than the first reference value offset_L.

In operation S411, when the DC offset is less than the first reference value offset_L, the DC offset calculator 140 outputs a bit value corresponding to a DC offset that has been increased with respect to the mean value of the ECG signal to the DAC 150. When the DC offset is determined as greater than the first reference value offset_L in operation S410, the DC offset calculator 140 determines whether the DC offset is less than a second reference value offset_H in operation S412.

In operation S413, when the DC offset is greater than the second reference value offset_H, the DC offset calculator 140 outputs a bit value corresponding to a DC offset that has been decreased with respect to the mean value of the ECG signal to the DAC 150. When the DC offset is determined as less than the second reference value offset_H in operation S412, the DC offset calculator 140 may perform operations S409 through S412 on a subsequent ECG signal.

Operations S401 through S407 illustrated in FIG. 4 are performed in the initial operation of the ECG sensor 10 (e.g., on the signal E1 in FIG. 3) and operations S409 through S413 may be repeated after the initial operation of the ECG sensor 10 (e.g., on signals E2, E3, and E4 in FIG. 3). Operations S401 through S407 may be performed based on a gain amplification value (or a reference gain amplification value) initially set by the automatic gain controller 130 and operations S409 through S413 may be performed while the gain amplification value is being adjusted by the automatic gain controller 130. The reference gain amplification value may be user defined and/or based on empirical evidence. At this time, a gain amplification value applied to the amplifier 110 in operations S403 through S407 may be less than a gain amplification value applied to the amplifier 110 in operations S409 through S413.

Figure 5:
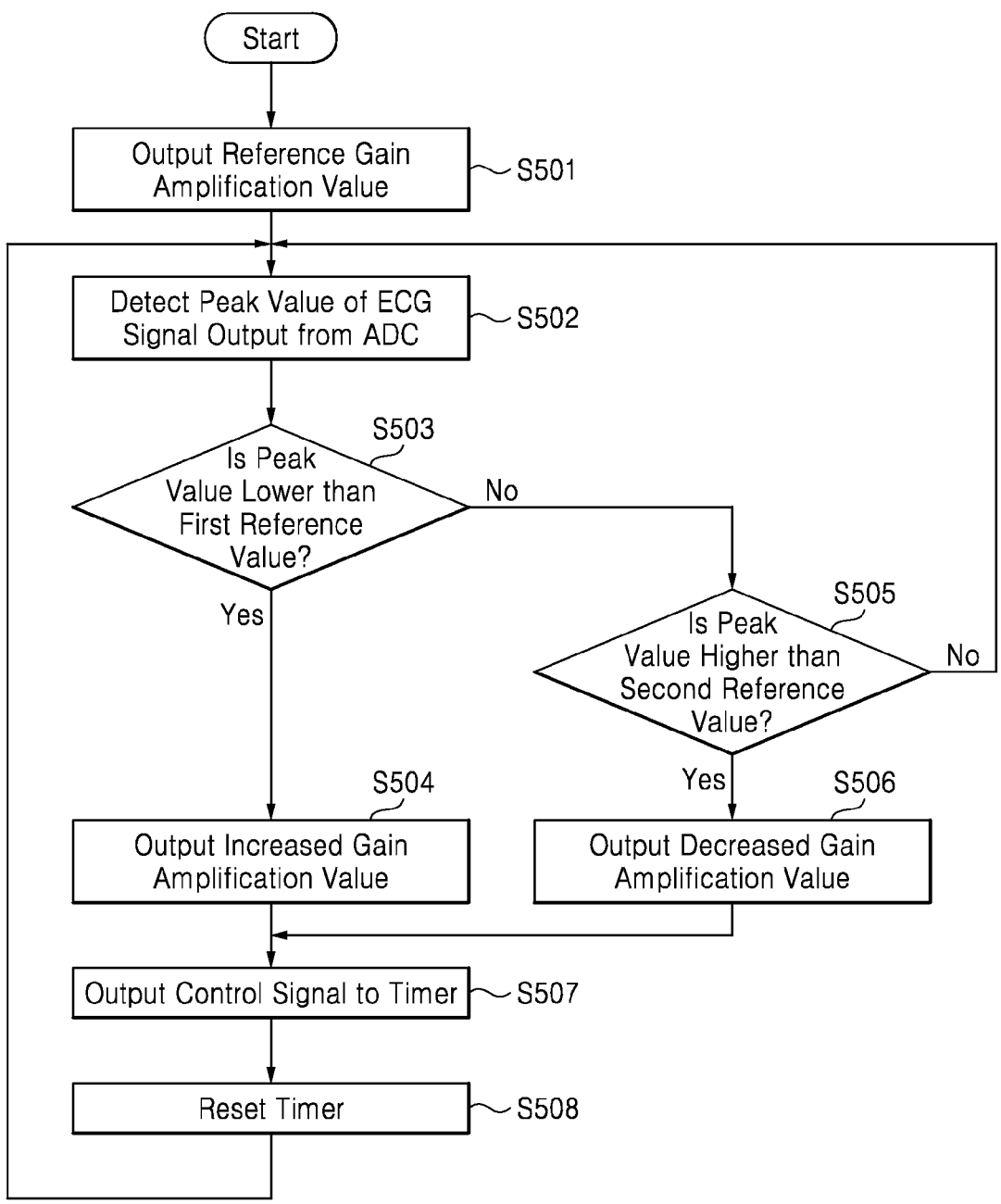
FIG. 5 is a flowchart of a method of processing a signal using an automatic gain controller illustrated in FIG. 2 according to at least one example embodiment of the inventive concepts.

FIG. 5 is a flowchart of a method of processing a signal using the automatic gain controller 130 illustrated in FIG. 2 according to at least one example embodiment of the inventive concepts. When receiving an ECG signal from the ADC 120 after the ECG sensor 10 starts and receiving the enable signal EN from the DC offset calculator 140, the automatic gain controller 130 may perform the method illustrated in FIG. 5.

Referring to FIGS. 2 through 5, the automatic gain controller 130 outputs an initially set reference gain amplification value to the amplifier 110 in operation S501. The automatic gain controller 130 detects a peak value of an ECG signal received from the ADC 120 in operation S502 and determines whether the peak value is lower than the first reference value min_level in operation S503.

In operation S504, when the peak value is lower than the first reference value min_level, the automatic gain controller 130 outputs a bit value corresponding to a gain amplification value that has been increased with respect to the ECG signal to the amplifier 110. In operation S505, when the peak value is determined as higher than the first reference value min_level, the automatic gain controller 130 determines whether the peak value is higher than the second reference value max_level.

In operation S506, when the peak value is higher than the second reference value max_level, the automatic gain controller 130 outputs a bit value corresponding to a gain amplification value that has been decreased with respect to the ECG signal to the amplifier 110.

In order to apply the gain amplification value that has been adjusted to the AFE 100 in operations S504 and S506, the automatic gain controller 130 outputs a control signal to a timer (not shown) in operation S507 so that a counting operation is performed based on desired (or alternatively, predetermined) time information. After the desired (or alternatively, predetermined) period of time, the automatic gain controller 130 resets the timer in operation S508.

Instead of performing operations S502 through S506, the automatic gain controller 130 may continuously output the adjusted gain amplification value to the amplifier 110 in operation S504 or S506.

The inventive concepts may also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices. The computer readable recording medium can also be distributed over network coupled computer systems so that the computer readable code is stored and executed in a distributed fashion. Also, functional programs, codes, and code segments for accomplishing the inventive concepts can be easily construed by programmers skilled in the art to which the inventive concepts pertain.

As described above, according to at least one example embodiment of the inventive concepts, an ECG sensor minimizes a DC offset and also automatically adjusts the gain of an amplifier, so that the magnitude of a measured ECG signal is maintained in a desired (or alternatively, predetermined) range. As a result, the ECG signal is detected more accurately.

While the inventive concepts have been particularly shown and described with reference to example embodiments thereof, it will be understood by those of ordinary skill in the art that various changes in forms and details may be made therein without departing from the spirit and scope of the inventive concepts as defined by the following claims.

What is claimed is:

1. An electrocardiogram (ECG) sensor comprising:
an analog front end device configured to,
remove a DC offset in a ECG signal received from a measuring electrode,
adjust a gain amplification value based on the ECG signal, and
output an adjusted ECG signal, the adjusted ECG signal being based on the adjusted gain amplification value and the removed DC offset in the ECG signal; and
a digital signal processor configured to detect information by analyzing and processing the adjusted ECG signal based on an algorithm and to output the information,
wherein the analog front end device is configured to,
remove the DC offset in a first ECG signal during a first period, and
remove a DC offset in a second ECG signal and adjust a gain amplification value for the second ECG signal during a second period, the gain amplification value for the second ECG signal being adjusted in response to an enable signal that is activated if the DC offset in the first ECG signal is within a first reference range.

2. The ECG sensor of claim 1, wherein the analog front end device comprises:
an amplifier configured to receive the ECG signal from the measuring electrode and amplify the ECG signal based on the gain amplification value for the ECG signal;
an analog-to-digital converter configured to perform analog-to-digital conversion on the amplified ECG signal and output a digital ECG signal; and
an automatic gain controller configured to detect a peak value of the digital ECG signal and to adjust the gain amplification value for the ECG signal based on the peak value.

3. The ECG sensor of claim 2, wherein the analog front end device further comprises:
a DC offset calculator configured to,
calculate a mean value of the digital ECG signal,
calculate a DC offset with respect to the mean value, and
output the DC offset calculated with respect to the mean value; and
a digital-to-analog converter configured to perform digital-to-analog conversion on the DC offset output from the DC offset calculator to output an analog DC offset,
wherein the amplifier is configured to remove the DC offset from the ECG signal based on the analog DC offset.

4. The ECG sensor of claim 3, wherein the DC offset calculator is configured to determine whether the DC offset calculated with respect to the mean value is in the first reference range.

5. The ECG sensor of claim 4, wherein the DC offset calculator is configured to output a bit value corresponding to a changed DC offset with respect to the digital ECG signal if the DC offset calculated with respect to the mean value is not in the first reference range, the bit value being output to the digital-to-analog converter.

6. The ECG sensor of claim 2, wherein the automatic gain controller is configured to detect the peak value of the digital ECG signal and to determine whether the detected peak value is in a second reference range.

7. The ECG sensor of claim 6, wherein the automatic gain controller is configured to output a bit value corresponding to a changed gain amplification value with respect to the digital ECG signal if the detected peak value is not in the second reference range, the bit value being output to the amplifier.

8. The ECG sensor of claim 2, wherein the automatic gain controller comprises a timer configured to count a time during which the adjusted gain amplification value is applied to one of the ECG signal and the second ECG signal.

9. The ECG sensor of claim 1, further comprising:
a radio frequency (RF) module configured to transmit the information detected by the digital signal processor via a wireless connection.

10. A method of processing a signal using an electrocardiogram (ECG) sensor, the method comprising:
- calculating, by the ECG sensor, a DC offset in a first ECG signal received from a measuring electrode during a first period;
- removing, by the ECG sensor, a DC offset from a second ECG signal received during a second period, the removing being based on the calculated DC offset in the first ECG signal; and
- calculating, by the ECG sensor, a DC offset in the second ECG signal received during the second period and adjusting a gain amplification value for the second ECG signal, wherein the calculating the DC offset in the second ECG signal and the adjusting the gain amplification value for the second ECG signal are performed simultaneously and repeatedly while the ECG sensor is operating.

11. The method of claim 10, wherein the calculating the DC offset in the second ECG signal comprises:
- calculating a DC offset with respect to a mean value of the second ECG signal;
- determining whether the DC offset is in a first reference range; and
- outputting a bit value corresponding to a decreased or increased DC offset with respect to the second ECG signal if the DC offset is not in the first reference range.

12. The method of claim 10, wherein the adjusting the gain amplification value for the second ECG signal comprises:
- detecting a peak value of the second ECG signal,
- determining whether the peak value is in a second reference range, and
- outputting a bit value corresponding to a decreased or increased gain amplification value with respect to the second ECG signal if the peak value is not in the second reference range.

13. An analog front end device, comprising:
- an amplifier configured to receive an ECG signal from a measuring electrode and amplify the ECG signal based on a gain amplification value;
- an analog-to-digital converter configured to perform analog-to-digital conversion on the amplified ECG signal and output a digital ECG signal;
- an automatic gain controller configured to adjust the gain amplification value for the digital ECG signal;
- a DC offset calculator configured to calculate a DC offset in the digital ECG signal and output the calculated DC offset; and
- a digital-to-analog converter configured to perform digital-to-analog conversion on the DC offset output from the DC offset calculator to output an analog DC offset,
- wherein the DC offset calculator configured to calculate a first DC offset in a first ECG signal, and the amplifier configured to remove the calculated first DC offset in a second ECG signal, the second ECG signal being received subsequent to the first ECG signal, and
- wherein the DC offset calculator configured to calculate a second DC offset in the second ECG signal, and the automatic gain controller configured to adjust an amplitude of the second ECG signal in response to an enable signal, the enable signal being controlled based on the calculated first DC offset.

14. The analog front end device of claim 13, wherein the automatic gain controller is configured to adjust the amplitude of the second ECG signal such that a peak value is within a first reference range.

15. The analog front end device of claim 14, wherein the automatic gain controller is configured to output a bit value corresponding to a changed gain amplification value with respect to the second ECG signal if the peak value is not in the first reference range, the bit value being output to the amplifier.

16. The analog front end device of claim 14, wherein the DC offset calculator is configured to calculate the second DC offset such that the second DC offset is within a second reference range.

17. The analog front end device of claim 16, wherein the DC offset calculator is configured to output a bit value corresponding to a changed DC offset with respect to the second ECG signal if the second DC offset is not in the second reference range, the bit value being output to the digital-to-analog converter.

18. The analog front end device of claim 13, wherein the DC offset calculator is configured to calculate the second DC offset based on a mean value of the second ECG signal.

19. The analog front end device of claim 18, wherein the amplifier is configured to remove a third DC offset in a third ECG signal based on the calculated second DC offset, the third ECG signal being received subsequent to the second ECG signal.

* * * * *